United States Patent [19]

Glassey

[11] Patent Number: 5,005,408
[45] Date of Patent: Apr. 9, 1991

[54] GAS WEIGHTS COMPENSATION METHOD FOR LIQUID DEPTH GAUGING SYSTEM

[75] Inventor: Eugene A. Glassey, San Diego, Calif.

[73] Assignee: Fluid Data Systems, San Diego, Calif.

[21] Appl. No.: 411,873

[22] Filed: Sep. 25, 1989

[51] Int. Cl.$^5$ .................. G01F 23/14; G01N 9/26
[52] U.S. Cl. ...................................... 73/301; 73/701; 73/708; 73/299
[58] Field of Search ............... 73/299, 302, 301, 701, 73/708

[56] References Cited

U.S. PATENT DOCUMENTS

| | | |
|---|---|---|
| 2,837,706 | 6/1958 | Glassey . |
| 3,002,382 | 10/1961 | Gardner .......................... 73/701 |
| 3,049,007 | 8/1962 | Joline ............................. 73/701 X |
| 3,089,502 | 5/1963 | Davidson et al. . |
| 3,186,423 | 6/1965 | Davidson et al. . |
| 3,232,091 | 2/1966 | Glassey . |
| 3,232,092 | 2/1966 | Glassey . |
| 3,256,740 | 6/1966 | Tate et al. ...................... 73/701 |
| 3,308,991 | 3/1967 | Glassey . |
| 3,323,368 | 6/1967 | Glassey . |
| 3,377,869 | 4/1968 | Glassey . |
| 3,407,664 | 10/1968 | Glassey . |
| 3,407,666 | 10/1968 | Glassey . |
| 3,475,959 | 11/1969 | Glassey . |
| 3,610,042 | 10/1971 | Brosius, Jr. ..................... 73/299 |
| 4,109,531 | 8/1978 | Lawford et al. ................ 73/301 X |
| 4,266,430 | 5/1981 | Glassey . |
| 4,274,039 | 6/1981 | Glassey . |
| 4,277,981 | 7/1981 | Glassey . |

FOREIGN PATENT DOCUMENTS 0141656 5/1978 Japan ................................ 73/701

OTHER PUBLICATIONS

Catalog entitled "Fluidgage", Fluid Data Systems, 1985, 11 pages.
Catalog entitled "Water Gage II", Fluid Data Systems, 4 pages.
Article entitled "Does Your Bubble Gage Give you the Right Answer?", WRD Bulletin, Jan.-Mar. 1974, by Winchell Smith.
Article entitled "Purge Gas Weight Etc." by Gene Glassey, 5 pages, Fluid Data Systems, 8 pages.
Article entitled "Level and Quantity Measurement" by Gene Glassey, Jun. 1987, 4 pages.

Primary Examiner—Daniel M. Yasich
Attorney, Agent, or Firm—Brown, Martin, Haller & McClain

[57] ABSTRACT

A method and apparatus for monitoring liquid levels using pressure responsive instruments is described, in which an arrangement for compensating for the effects of errors including gas weights errors is provided. The required compensation factor for a particular installation is first calculated theoretically, and then used in order to raise the output signal of the instrument electronically by the calculated factor. In one arrangement, the output signal is amplified by the desired factor. Alternatively, the excitation voltage of the instrument itself, or of a potentiometer used to interface the instrument to electronic data acquisition devices, is varied in order to raise its output voltage by the desired compensation factor.

16 Claims, 3 Drawing Sheets

FIG. 3
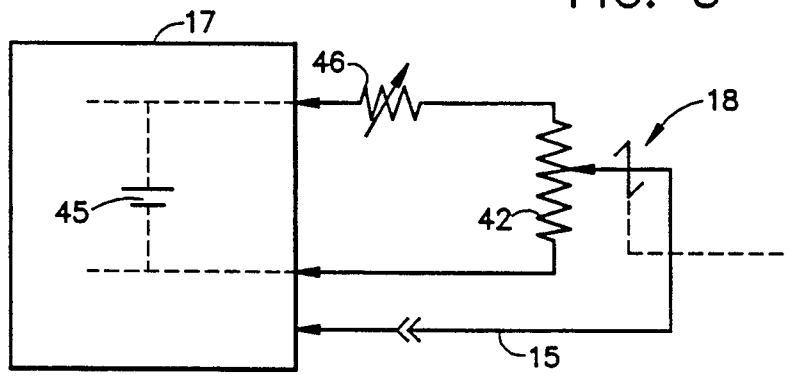
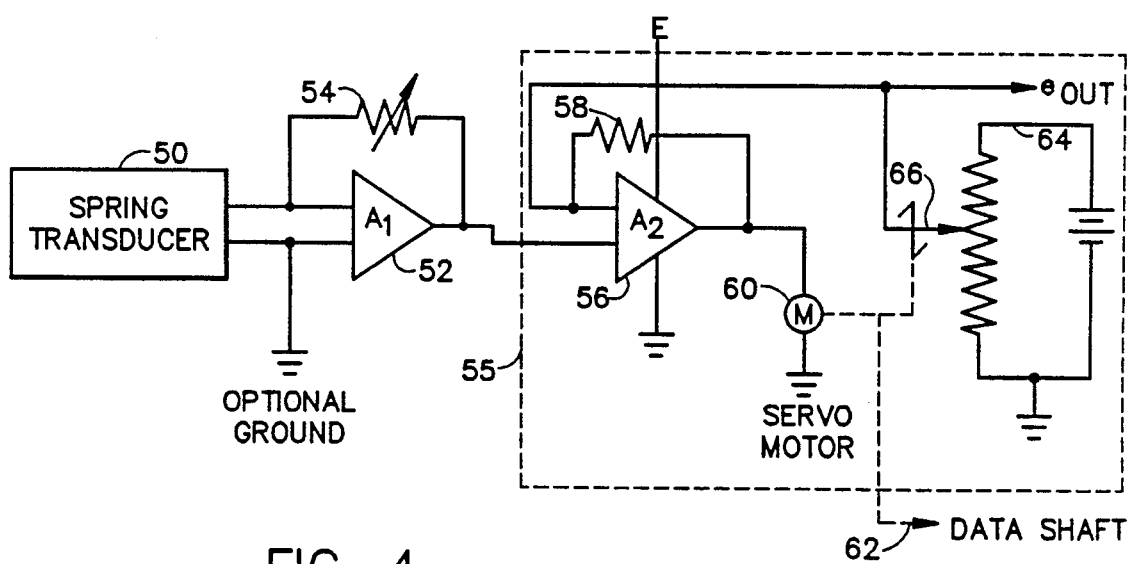
FIG. 4

GAS WEIGHTS COMPENSATION METHOD FOR LIQUID DEPTH GAUGING SYSTEM

BACKGROUND OF THE INVENTION

The present invention relates generally to the monitoring or gauging of hydrostatic pressure, and more particularly to a compensation method for use in such systems to improve accuracy.

Various instruments are known for monitoring liquid levels in tanks, reservoirs and the like. One category of liquid monitoring instrument is responsive to changes of hydrostatic pressure at a submerged level in the liquid. In most cases, a so-called "bubbler system" is connected to the instrument, in which a small diameter tube runs from an instrument shelter above the water or liquid surface to a reference elevation near the bottom of the water. The lower end of the tube is, most often, secured slightly below the lowest anticipated liquid level. A trace flow of pressurized gas is passed down the tube, escaping as bubbles at the lower end. The pressure of gas at the lower end of the tube is equal to the hydrostatic pressure of the liquid at the submerged horizontal reference plane of the lower end of the tube. A suitable pressure responsive instrument or gauge is connected to measure the resultant gas pressure at a convenient elevation above the liquid. However, this pressure will not be identical to that at the lower end of the tube due to the vertical component of the weight of the gas in bubbler line. In fact, the pressure measured by the gauge (gauge pressure) will be lower than the hydrostatic pressure of the liquid at the submerged reference plane by an amount equal to the vertical component of the weight of the gas in the bubbler line. Also, for best accuracy, since the water or liquid filling the tank or reservoir displaces the atmosphere, compensation should be made for the vertical component of the displaced atmosphere, for the best accuracy. Other corrections, such as a correction for the local gravitational variation, may be necessary, dependent on the nature of the pressure responsive instrument itself.

A gas-weights compensation equation has been developed by the applicant in order to facilitate making these corrections in a pressure responsive instrument. This compensation has been employed for some time in "balanced beam manometer" types of pressure responsive instruments. Various instruments of the balanced beam manometer type are described in my U.S. Pat. Nos. 4,266,430, 4,274,039 and 4,277,981. In this type of instrument, gas weights and other compensations have been made by altering the calibration slope of the instrument slightly to cause it to read "high" by an amount equal to the applicable correction. This has been accomplished in the past by changing the poise weight, for example making the weight one percent low so that the instrument will read one percent high, and adding trim weights to the poise to adjust the calibration to a particular site.

SUMMARY OF THE INVENTION

It is an object of this invention to provide an alternative method and apparatus for incorporating gas weights compensations in both balanced beam and other types of pressure responsive instruments or gauges, for example strain gauge pressure transducers.

According to a first aspect of the present invention, a method of compensating for the effects of gas weights in a pressure responsive instrument for measuring hydrostatic pressure, usually used as "inferred" liquid level, is provided, which comprises the steps of calculating a gas weights compensation factor and electronically increasing the output voltage of the pressure responsive instrument by the calculated amount. The output voltage may simply be increased by amplifying the output signal of the instrument by the desired compensation factor. Alternatively, the excitation or input voltage of the instrument may be elevated until the output is elevated by the prescribed amount. In a balanced beam type instrument where the data shaft controls the output of a potentiometer for interfacing the instrument to a suitable electronic data acquisition system or device, the input voltage to the potentiometer may be varied so that the output signal from the potentiometer is raised by the desired factor. Where the data acquisition device connected to the potentiometer output has its own internal reference voltage source to which the measured voltage is compared, this source may itself be used as the potentiometer excitation, with a trimming resistor between the input and the potentiometer to yield the desired compensation factor in the potentiometer output signal.

In a spring opposed pressure transducer of the potentiometeric or strain gauge type whose output for a given pressure is proportional to its excitation voltage, the excitation voltage may be elevated by an amount necessary to increase its output voltage by the desired factor. A variable voltage input may be provided for this purpose.

Alternatively, the output signal from a conventional pressure transducer may be amplified by means of an amplifier having the desired amplification factor. The amplifier may have a variable feedback resistance to allow the amplification factor to be varied according to the calculated gas weights compensation factor. In another alternative, the input or excitation voltage of a strain gauge type pressure transducer may be elevated by a predetermined factor so that the output is elevated by an amount greater than the desired compensation, and a variable resistance may be provided at the output to reduce the output to a level corresponding to the desired compensation factor. In the case of a spring restored transducer, the compensation will include an earth gravity correction factor in addition to the gas weights compensation factors, in order to compensate for local gravity variations.

This method provides a convenient means for compensating for various error sources in measuring liquid levels, providing a much more accurate end result in liquid level monitoring systems.

According to another aspect of the present invention, a pressure responsive, hydrostatic pressure monitoring system is provided, which comprises a pressure responsive instrument having an input for connection to a quantity of liquid to be monitored and a signal output proportional to the pressure applied to its input, an interface arrangement for connecting the instrument input to the liquid to be measured in order to apply a pressure dependent on the liquid pressure to the instrument, a data acquisition device connected to the signal output of the instrument for monitoring the hydrostatic pressure, and a variable electrical compensation device for varying the signal output of the instrument by a predetermined amount corresponding to at least a calculated gas weights compensation factor.

The compensation factor will be dependent on the actual installation site, the type of pressure responsive instrument used and on the interface arrangement between the instrument and the liquid being measured. Where the interface arrangement is of the so-called "bubbler" type in which the instrument is located above the level of the liquid and connected to the liquid via a bubbler line running to a reference location near the bottom of the liquid, the compensation factor includes a correction for the weight of the gas in the bubbler line as well as a correction for the displaced atmosphere. Where the pressure instrument can be physically located below the measured liquid or located outside a tank close to the bottom, so that the liquid pressure can be applied directly to the instrument with no vertical displacement, the compensation factor does not need to include any correction for the weight of a column of purge gas and will then include a correction for displaced atmosphere. The compensation factor may also include a correction for local earth gravity variations where spring restored pressure transducers are used.

BRIEF DESCRIPTION OF THE DRAWINGS

The present invention will be better understood from the following detailed description of some preferred embodiments thereof, taken in conjunction with the accompanying drawings, in which like reference numerals refer to like parts, and in which:

FIG. 3 illustrates a modification of the system of FIG. 1;

FIG. 4 is a schematic block diagram illustrating a second embodiment of the invention;

DESCRIPTION OF THE PREFERRED EMBODIMENTS

Figure 1:
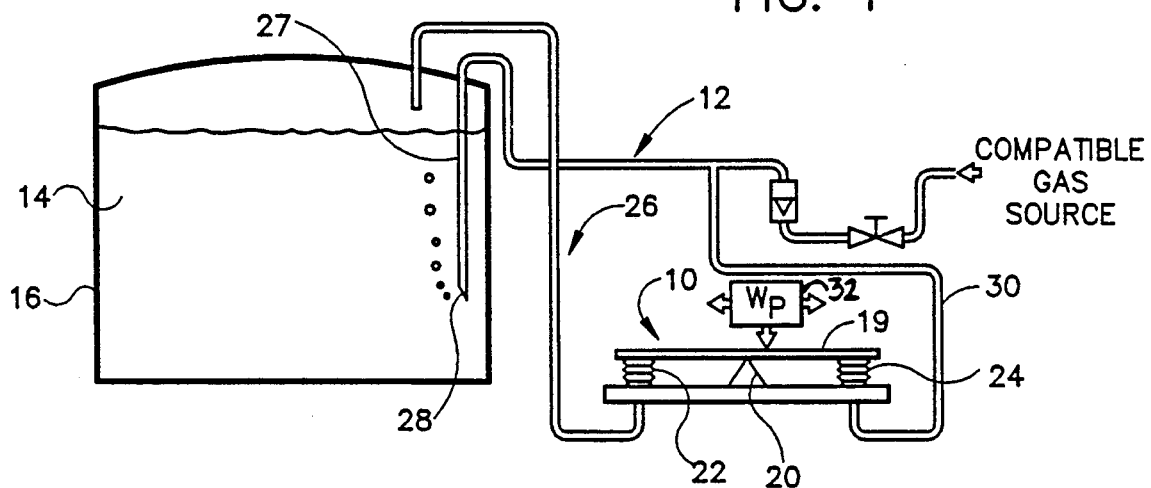
FIG. 1 is a schematic view of one form of pressure responsive instrument employing a bubbler system to measure the hydrostatic pressure or inferred height of a liquid.
Figure 2:
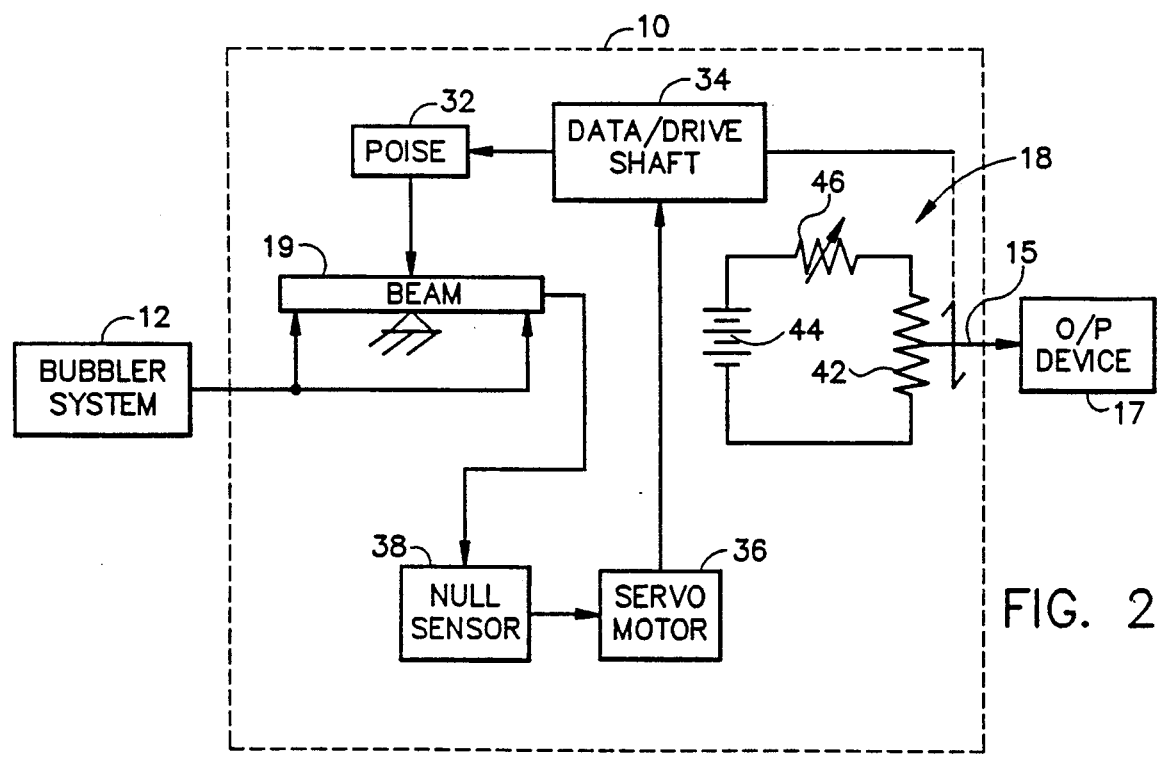
FIG. 2 is a schematic block diagram illustrating a system for measuring hydrostatic pressure or inferred liquid level including a device for introducing an error compensation factor according to a first embodiment of the present invention.

FIGS. 1 and 2 illustrate a pressure responsive hydrostatic pressure or inferred liquid level monitoring system incorporating a gas weights compensation means according to a first embodiment of the present invention. The system basically comprises a pressure responsive instrument 10 of the balanced beam manometer type connected via an interface device such as bubbler system 12 to a quantity of liquid 14 in a tank 16 in order to monitor the level of the liquid. Although the instrument is illustrated in FIG. 1 as monitoring the level of liquid in a tank, it will be understood that similar systems are utilized for monitoring the levels of other bodies of liquid, such as reservoirs, rivers, and ground water. As schematically illustrated in FIG. 2, the output 15 of the instrument 10 is connected to drive a suitable output device 17 such as an electronic data logger, recorder, transmitter or the like as is known in the field. A variable compensation factor is introduced into the output signal at output 15 which elevates the output signal by a calculated amount, as will be explained in more detail below.

The balanced beam manometer 10 is a servo-balanced instrument, like a beam balance or scale for weighing, but with the weigh-pan replaced by an instrument bellows that exerts force on the beam. The instrument comprises a beam 19 balanced on a fulcrum 20 with pressures applied at opposite ends of the beam via bellows 22,24. Bellows 22 is connected via line 27 to a tank-dome, reference, pressure above the body of liquid, while bellows 24 is connected to the bubbler system 12. A bubbler line 26 runs from a valved source of pressurized gas, such as nitrogen, to a location 28 near the bottom of the tank 16. The pressure in the bubbler line is applied to bellows 24 via line 30. A poise 32 is slidably mounted on the beam 19 to counterbalance the force applied from the bubbler line.

For purposes of illustration in FIG. 1, the balanced beam manometer is shown near the ground level of the tank, as in tank gauging. In hydrostatic water-stage gauging, the instruments must usually be well above the highest waterstage or level. The subject gas-weight correction would be much larger in this case.

As schematically illustrated in FIG. 2, poise 32 is driven along the beam 19 by means of a data shaft 34 rotated by servo-motor 36, while the servo-motor itself is controlled by the output of null sensor 38 which detects the null, or balanced, position of the beam 19. Tilting of the beam 19 as a result of pressure applied from the bubbler system will be detected by the null sensor, resulting in operation of the servo motor 36 to rotate data shaft 34 to drive the poise along the beam until the beam is again balanced. Thus, the rotation of the data shaft is proportional to the applied pressure. A mechanical counter (not illustrated) is conventionally connected to the data shaft. In the preferred embodiment of the inventions, these components of the balanced beam manometer 10 are essentially the same as described in my U.S. Pat. Nos. 4,266,430 and 4,277,981, and will therefore not be described in any greater detail here.

As schematically illustrated in FIG. 2, the data shaft is also connected to control a drive circuit 18 producing the output signal 15. Drive circuit 18 includes a potentiometer 42 to produce an analog output signal to interface the instrument to the output device 17. Potentiometer 42 has a suitable power supply 44, and a variable trimming resistor 46 is connected between the power supply 44 and the potentiometer in order to vary the potentiometer voltage, and thus the output signal, by a desired compensation factor. The potentiometer may be mounted within the same housing as the remainder of the pressure responsive instrument 10, and may have its own internal power supply, as illustrated in FIG. 2. Alternatively, a reference supply 45 in the output device 17 may itself be used as the power supply for potentiometer 42, as illustrated in FIG. 3. Most solid state electronic data acquisition devices have an internal reference voltage source to which measured input voltages are compared, and this internal supply is often made available for use in powering auxiliary devices. If output device 17 has an internal supply of this type, this supply may be connected to the potentiometer 42 as indicated in FIG. 3.

The supply voltage of the potentiometer corresponds to full scale travel of the potentiometer, which in turn is proportional to a predetermined input pressure to the manometer, and thus a predetermined water depth. By varying the voltage across the potentiometer, the output voltage for a predetermined liquid depth will also be varied, allowing a predetermined compensation factor to be added. For example, assume that the potentiometer is of ten turns full scale, and is driven 10 turns for 4800 counts or units full-scale corresponding to 48 feet. If the supply voltage were 4.8 Volts, the potentiometer would yield one millivolt per 0.01 foot as the compensated analog output voltage. However, the supply voltage in this example is arranged to be higher than this, for example 5 Volts, while the resistor is arranged to attenuate the input voltage to some discrete value less than 5 but greater than 4.8, using an attenuation factor equal to the desired compensation factor. In other words, the output signal will be higher by the desired compensation factor.

The compensation factor is arranged to make any desired corrections in the output signal according to various factors, dependent on the particular installation. In the installation as illustrated in FIGS. 1 and 2, the pressure of gas at the lower tip of the tube or bubbler line from which bubbles of gas escape is equal to the hydrostatic pressure of the water at the horizontal reference plane of the tip. This pressure is in turn proportional to the height, or level of water in the tank at a given water temperature. The pressure in the bubbler line at the higher elevation where the measuring instrument is located will be equal to this hydrostatic pressure minus the vertical component of the weight of gas in the bubbler line and minus a component corresponding to the atmosphere displaced by the liquid in the tank. These components are generally referred to as "gas weights" compensations. Thus, for accurate results, the gauge pressure must be compensated by adding to it a term corresponding to a calculated gas weights compensation factor in order to provide an output equivalent to the actual hydrostatic pressure at the level of the bubbler line tip.

The approximate error compensation factor for a particular installation may be calculated from the following relationship:

$$P_g = D_w(H_h - H_r) - D_n \frac{D_w(H_h - H_r) + P_z}{P_o}(H_i - H_r) - D_z(H_h - H_r) \quad (1)$$

| In Which: | UNITS |
|---|---|
| $P_g$ = Pressure of the purge gas analog of depth (Gauge), | $Kg/M^2$ |
| $D_w$ = Density of gauged water, assume unity, (1000 $Kg/M^3$) | 1000 $Kg/M^3$ |
| $H_h$ = Height of water, (For convenience use maximum stage, or maximum possible liquid depth) | Meters above sea level |
| $H_r$ = Height of reference, (Bubbler level), (Choose z = $H_r$) | Meters above sea level |
| $H_i$ = Highest point of bubbler line (Apex, usually in proximity of plumbing Tee to instruments.) | Meters above sea level |
| $P_z$ = Local atmospheric pressure at elevation z. | From Equation 3, below |
| $P_o$ = Standard atmosphere pressure at sea level, o | 10,322 $Kg/M^2$ |
| $D_z$ = Local density of air at pressure $P_z$, | From Equation 2, below |
| $D_o$ = Standard atmosphere density of sea level, o | 1.226 $Kg/M^3$ |
| $D_n$ = Standard nitrogen density at sea level, | 1,250 $Kg/M^3$ |
| o = Sea level elevation reference | Zero |
| z = Station elevation above sea level. | Meters |

$$P_g = D_w(H_h - H_r) - D_n \frac{D_w(H_h - H_r) + P_z}{P_o}(H_i - H_r) - D_z(H_h - H_r) \quad (1)$$

(Choose z = $H_r$)

Formulas for the weights and pressures of atmospheric air at elevations above the standard sea level reference of the Standard Atmosphere are as follows:

$$D_z = [(288 - 0.0065z)/288]^{4.256} \times 1.226 \, Kg/M^3, \, Kg/M^3 \quad (2)$$

$$P_z = [(288 - 0.0065z)/288]^{5.256} \times 10332 \, Kg/M^3 \, Kg/M^2 \quad (3)$$

References: Formulas 2. and 3. are from Smithsonian Meteorological Tables, Sixth Edition, Table 63, Titled "ICAN (International Commission for Air Navigation) Standard Atmosphere."

Equation (1) above may be described in simple words. The gauge pressure, $P_g$, on the left is said to be equal to the hydrostatic pressure of the water (the first term on the right), minus the pressure created by the weight of the purge gas column, (the second term on the right), minus the buoyancy exerted by the displacement of the atmosphere by the water, (the third and last term on the right). The reference elevation (z) is the horizontal plane of the bubbler orifice.

The first term on the right is the dominant term and says that the pressure at that elevation is equal to the depth of water times its density. This is representative of the analog pressure of bubbler systems that do not incorporate the subject corrections and the value that is generally employed due to lack of understanding the corrections. Typically, this introduces an error that approximates ½% to 1%, but can be larger with deep reservoirs or pressurized vessels.

Bypassing the second term on the right for the present, the third is also simple: The buoyancy given to the water by the atmosphere is equal to the density of the air times the volume of air displaced as the water rises from reference elevation, $H_r$, to some arbitrary level, $H_h$. The analysis is simplified by assuming this to be the "highest" or full-scale level. This, also, represents the "worst case" condition. We must, however, know the density of the air $D_z$ at the altitude of the gauging station. This information can be calculated for a particular site using Equation 2., which is a standard equation for atmospheric density vs elevation above sea level. Its accuracy, and that of equation 3., are exceedingly well proved in aviation, for example, as a reference for the calibration of altimeters and other atmospheric pressure actuated aircraft instruments. (Standard Atmosphere.)

Referring now to the second term on the right of equation (1), this refers to the correction for the pressure created by the column of gas in the bubbler line the so-called "gas-weights" error. As an aid in visualization, the column of relatively heavy compressed gas in the bubbler line projecting out of the water may be compared to the weight of the exposed stem of a hydrometer in the water surface, whose weight bears downward in similar manner.

By the universal gas law, we know gas density varies inversely with pressure for a constant volume of gas at constant temperature. The portion of the second term in brackets represents the compression ratio for the commonly employed nitrogen gas in the bubbler line. The denominator is the pressure at standard atmosphere and numerator is the pressure under the prevailing conditions; the hydrostatic pressure of the water plus the atmosphere above. This ratio is multiplied by the standard density, $D_n$, and subsequently by the net height of the nitrogen column to get the pressure exerted by the column.

Equation (1) may also be expressed in terms of absolute units, where $P_a$ equals absolute pressure on the left side of the equation, as follows:

$$P_a = D_w(H_h - H_r) - \tag{4}$$

$$D_n \frac{D_w(H_h - H_r) + P_z}{P_o}(H_i - H_r) - D_z(H_h - H_r) + P_z$$

We have simply added local barometric pressure to the end of the equation and to $P_g$ on the left side to yield $P_a$, since absolute pressure equals gauge pressure plus barometric pressure.

Strictly speaking, the density of nitrogen yielded by the second term on the right is the density at the orifice. This value would be slightly greater than the implied average value, because of the weight of the gas itself causing some added compression progressively down the line. The difference is negligible except for rare instances. Also, barometric pressure is treated as uniform over the small excursion of the level change.

Equations (1) and (4) apply to pressure responsive instruments such as balanced beam manometers and liquid filled manometers which are not influenced by local earth gravity variations. For other pressure responsive instruments, such as spring restored pressure transducers, which are subject to earth gravity variations, a gravity compensation factor may be added to the equation, as will be explained in more detail below.

The calculation of a gas weights compensation factor or coefficient for a balanced beam manometer at a hypothetical installation will now be explained by way of example.

Assume a hypothetical case of a water reservoir of 90 Meters storage depth capacity, measured above the bubbler orifice. Assume the instrumentation is located 6 additional meters above maximum stage. To avoid ambiguities, this is the apex of the bubbler line, at which a plumbing Tee is located to supply the pressure analog to the pressure responsive instrument(s). The elevation of the bubbler orifice is 800 meters above sea level.

Therefore: $z = H_r = 800$ Meters, $H_h = 890$ Meters and $H_i = 896$ Meters.

First, the local air density and barometric pressure at elevation z are calculated as follows:

$D_z = [(288 - 0.0065 \times 800)/288]^{4.256} \times 1.226 = [(0.981-94)]^{4.256} \times 1.226 = 0.92538 \times 1.266 = 1.1345$ Kg/M$^3$ $P_z = [(288 - 0.0065 \times 800)/288]^{53256} \times 10,332$ Kg/M$^2 = [(0.98194)]^{5.256} \times 10,322 = 0.9864 \times 10,322 = 9,388$ Kg/M$^2$ Substituting these values in original Equation 1:

$$P_g = 1000(890 - 800) - 1.250\frac{1000(890 - 800) + 9388}{10,332}$$
$$(896 - 800) - 1.1345(890 - 800)$$
$$= 90,000 - 1.250\frac{90,000 + 9388}{10,332} 96 - 1.1345 \times 90$$
$$= 90,000 - 1.250(9.6194)96 - 102.105$$
$$= 90,000 - 1154.33 - 102.105$$

Dividing by 1000 to convert Kg/M$^3$ weight to equivalent meters depth,

Meters depth indicated $= 90 - 1.154 - 0.102 = 88.74$ Meters for 90 meters actual.

Error compensation factor $= 90/88.74 = 1.0142$ or approx 1.42%.

Once the error compensation factor for a particular site utilizing the system illustrated in FIG. 2 has been calculated in the manner outlined above, the variable resistance can be adjusted to provide the specified percentage increase in the output signal in order to correct the liquid level measured by the output device or recorder by the desired factor. This produces a very accurate result in an inexpensive and relatively simple manner.

The method described above in connection with FIG. 2 may be used in any servoed type of instrument employed in hydrology which has proportional shaft position outputs which can be used to position potentiometer shafts, including balanced beam manometers as described above as well as servoed forms of mercury manometers which are commonly employed in hydrology.

FIG. 4 of the drawings illustrates a method and apparatus for introducing a calculated compensation factor including gas weights compensation into the output of a spring restored, pressure responsive transducer 50 of the type sometimes used in measuring liquid depth or level in various hydrological applications. This type of transducer is well known in the field, and uses elastic or spring members to oppose the force exerted by the measured pressure, which may be applied to the transducer via a bubbler system as in FIG. 1, for example. Some examples of this type of transducer are the Bourdon tube or bellows actuated potentiometer transducer, the resistance strain gauge transducers and resonant type quartz transducers, especially as manufactured by Paro Scientific, Redmond, Wash.

The compensation factor for a particular site will be calculated as described above, including a gravitational correction in the standard manner used for such transducers as well as the gas weights compensation terms of equation 1 where the transducer is connected to a bubbler system and located above the body of liquid. Where the transducer can be located physically below the liquid, for example downstream from a dam or beneath a tank, or can be submerged at the bottom of a river or tank so that liquid pressure is applied directly to the instrument, the compensation will be calculated without the second term on the right of Equation (1), employing only the displaced atmosphere compensation term. However, instances where transducers can be physically submerged are limited, in view of potential covering by silt deposition, interference of surface ice, risk of loss during floods, and so on. Additionally, in some cases the transducer can be located outside a tank, near its bottom, and connected to the tank by a substantially horizontal pressure line, also eliminating the need for the compensation for the weight of a vertical column of gas as in Equation (1). Also, the system illustrated in FIG. 2 may in some cases be located below the liquid level, for example downstream of a water reservoir. In these cases a hydrostatic pressure line may be plumbed directly to transducer 50 or to bellows 24. In these cases the compensation factor or coefficient will also be calculated using Equation (1) without the second term on the right and adding a gravitational correction on the right if necessary.

In FIG. 4, the output of transducer 50 is amplified by means of operational amplifier 52 which has a variable feedback resistance 54 for controlling the gain of the amplifier by the calculated coefficient. The gain may be adjusted simply by connecting two digital voltmeters to the test points at the input and output of amplifier 52 and adjusting feedback resistor 54 until the requisite ratio of values is obtained. In practice, a gain of slightly more than 1 will be needed. Thus, for example, the variable feedback resistance 54 may be designed to cover a range of gain from 1.0000 to 1.0200.

The output of amplifier 52 is connected to an interface circuit 55 for connection to any standard hydrologic data acquisition device or combination of devices. In FIG. 4, the interface circuit allows connection to a potentiometer driven data encoder as well as to a mechanical data shaft driven output device. Interface circuit 55 comprises a second amplifier 56 having an input connected to the output of amplifier 52 and a feedback resistance 58. The output of amplifier 56 is used to operate a servo motor 60 which is illustrated as driving a mechanical data shaft 62 which can be used to drive all types of traditional hydrologic shaft driven recorders and transmitters. Additionally, an optional output potentiometer 64 is provided, which is designed to interface with electronic data acquisition systems. The slider 66 of potentiometer 64 is positioned by the output of servo motor 60.

Figure 5:
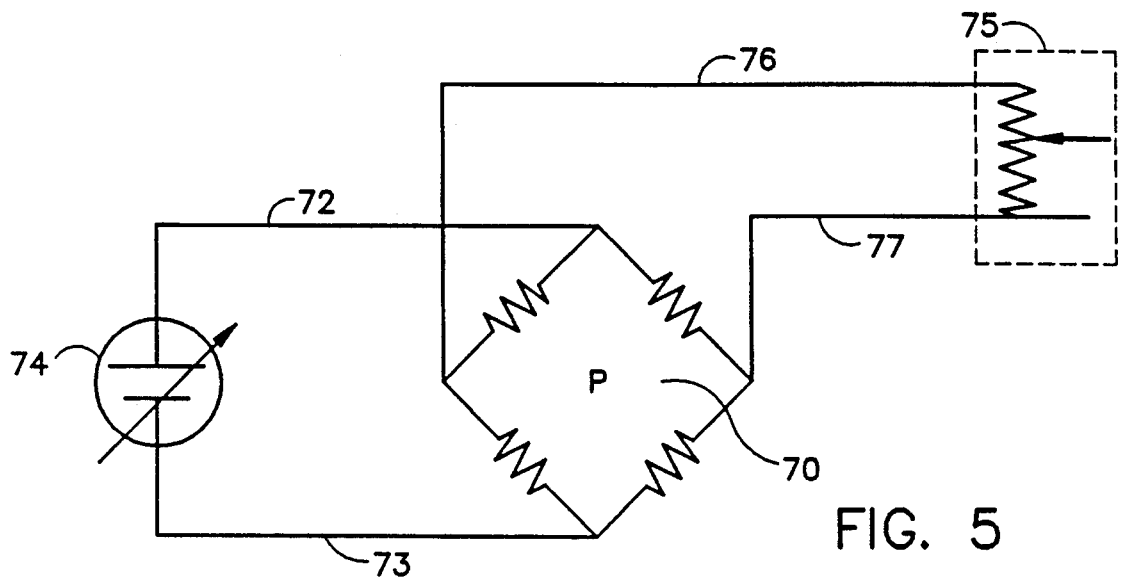
FIG. 5 is a schematic block diagram illustrating a third embodiment of the invention.

FIG. 5 illustrates an alternative method for compensating for gas weights and other potential errors in a pressure transducer of the resistance strain gauge or Wheatstone bridge type. As illustrated in FIG. 5, strain gauge transducer 70 has an excitation or input voltage applied across lines 72,73 to two opposite diagonal points of the bridge from a variable voltage source 74. A suitable measuring instrument 75 is connected across lines 76,77 connected to the other two diagonal points of the bridge to measure changes in signal voltage resulting from strain or pressure applied to the transducer, which will be proportional to the water or liquid level. The excitation voltage is varied by the amount necessary to produce the necessary elevation in the output signal, according to the calculated compensation factor or coefficient.

Figure 6:
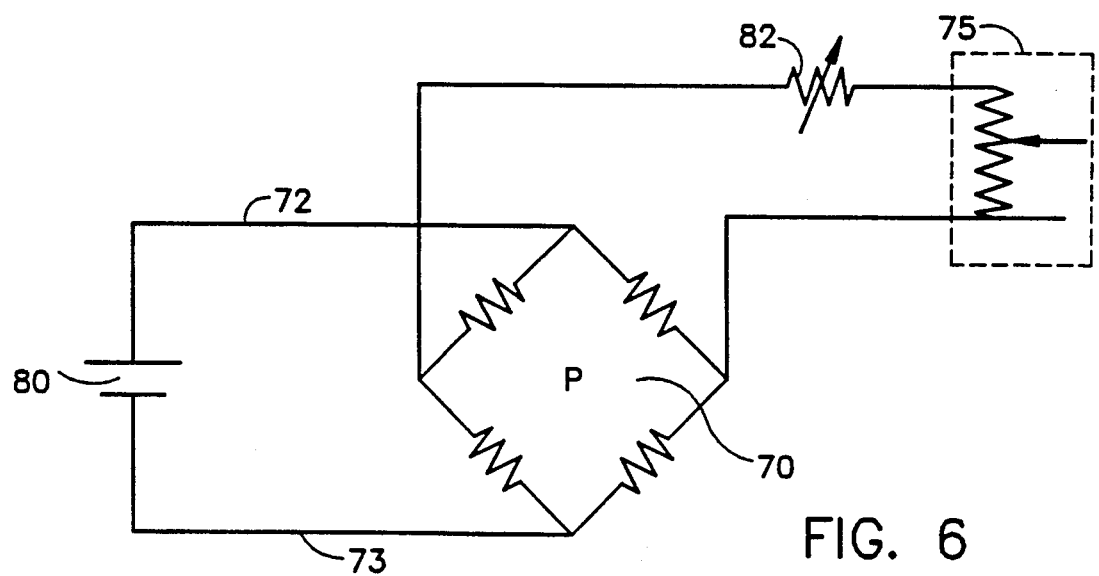
FIG. 6 is a schematic block diagram illustrating a fourth embodiment of the invention.

FIG. 6 illustrates a modification of the apparatus of FIG. 5, in which the strain gauge transducer 70 has a constant input voltage supply 80 which is arranged to be higher than the standard input voltage to such transducers by an amount sufficient to increase the output voltage to read high by an amount greater than the maximum anticipated compensation coefficient. For example, the input voltage may be 1% higher than normal. A variable resistance 82 is connected in output line 76 in order to vary the output voltage to correspond the desired compensated value. The resistance 82 is varied until the output signal is lowered to the desired compensated value.

The compensation methods described above are improvements over the known compensation technique in which the poise weight of a balanced beam manometer is varied to produce the desired compensation, since they can be applied to all types of pressure responsive instruments, not only balanced beam manometers, and also since they are convenient, inexpensive, and simple to adjust. Existing instruments can be easily modified to allow gas weight compensation adjustments as described above, producing much more accurate results. It has been established that gas weights errors can be very significant, dependent on the nature of the installation, and typically are of the order of $\frac{1}{2}$ to 1%, and may be even larger with deep reservoirs or pressurized vessels. The invention provides a convenient and inexpensive means for correcting such errors, in any type of pressure responsive instruments, which can be easily customized to any particular installation.

Although some preferred embodiments of the present invention have been described above by way of example only, it will be understood by those skilled in the field that modifications may be made to the disclosed embodiments without departing from the scope of the invention, which is defined by the appended claims.

I claim:

1. A method of measuring a liquid level in a body of liquid, comprising the steps of:

sensing the hydrostatic pressure at a submerged level close to the bottom of a body of liquid to produce a pressure signal dependent on said hydrostatic pressure;

applying the pressure signal as an input to a pressure responsive instrument having an output proportional to the pressure input;

calculating an error compensation factor to compensate for predetermined errors in the pressure signal including gas-weights errors;

connecting the output signal of the pressure responsive instrument to compensation means for amplifying the output by said calculated compensation factor; and connecting the amplified output to a data acquisition means for monitoring said hydrostatic pressure.

2. The method as claimed in claim 1, wherein the output signal is increased by amplifying the output voltage of the instrument by the calculated amount.

3. The method as claimed in claim 1, wherein the input voltage to a potentiometer providing an analog voltage output from a pressure responsive instrument to a data acquisition instrument is varied to increase the output voltage by the calculated amount.

4. The method as claimed in claim 3, wherein the input voltage is varied by connecting a variable resistance between an input voltage to the potentiometer and the potentiometer.

5. The method as claimed in claim 1, wherein the output signal is increased by varying the excitation voltage of a pressure responsive transducer by an amount sufficient to raise its output voltage by the calculated amount.

6. The method as claimed in claim 1, wherein the step of increasing the output voltage comprises increasing the excitation voltage of a pressure responsive transducer by an amount sufficient to raise its output voltage by an amount greater than the calculated amount, connecting a variable resistance to the output of the transducer, and varying the resistance to reduce the output voltage to the calculated compensation level.

7. A pressure responsive liquid level measuring system, comprising:
- a pressure sensing device having a pressure signal dependent on the hydrostatic pressure at a submerged level in a body of liquid to be monitored;
- a pressure responsive instrument having an input for connection to said pressure signal and a signal output proportional to the pressure applied at its input;
- drive means responsive to said signal output for producing an output voltage drive signal for driving a data acquisition device;
- said drive means including variable electrical compensation means for varying said drive signal by a predetermined amount corresponding to a predetermined compensation factor including gas weights error.

8. The system as claimed in claim 7, wherein said pressure responsive instrument comprises a balanced beam manometer having an output data shaft, and said drive means includes a potentiometer, connecting means connecting said output data shaft to said potentiometer to control the position of the potentiometer slider, an input voltage supply of a predetermined value connected across said potentiometer, said data acquisition device being connected tc the output of said potentiometer, and said electrical compensation means comprises means for varying said input voltage by the predetermined compensation factor.

9. The system as claimed in claim 8, wherein the means for varying said input voltage comprises a variable resistance connected between said input voltage supply and said potentiometer.

10. The system as claimed in claim 9, wherein said input voltage supply comprises an internal voltage reference of said data acquisition means.

11. The system as claimed in claim 8, wherein the input voltage supply is 5 Volts and the potentiometer is a 10 turn potentiometer having a full scale travel corresponding to 48 feet.

12. A pressure responsive liquid level measuring system for measuring the level of a body of liquid, comprising:
- a bubbler device for sensing the hydrostatic pressure at a submerged level in the body of liquid and producing an output pressure signal dependent on said hydrostatic pressure;
- a spring restored pressure transducer connected to said bubbler device and having input means for application of the output pressure signal to the transducer and output means for producing an output voltage dependent on said output pressure signal;
- compensation means for changing said output voltage by a predetermined compensation factor to produce a compensated output signal; and
- readout means driven by said compensated output signal to provide a reading indicating said hydrostatic pressure.

13. The system as claimed in claim 12, wherein said compensation means comprises a variable voltage source connected to said input terminals for varying the excitation voltage by an amount sufficient to raise the output voltage at said output terminals by said predetermined amount.

14. The system as claimed in claim 12, wherein said compensation means comprises a fixed voltage source of value greater than said predetermined excitation voltage connected across said input terminals for increasing the output voltage at said output terminals by an amount greater than said predetermined amount, and variable resistor means connected to said output terminals for reducing said increase in said output voltage to an amount corresponding to said predetermined amount.

15. The system as claimed in claim 12, wherein said compensation means comprises an amplifier connected to the output terminals of said transducer, the amplifier having a variable feedback resistance for varying the gain of said amplifier by an amount corresponding to said predetermined amount.

16. A pressure responsive liquid level measuring system for measuring the level of a body of liquid, comprising:
- a bubbler means communicating with the body of liquid at a submerged level for producing a pressure signal dependent on the hydrostatic pressure at said submerged level, said pressure signal including predetermined errors including gas-weights errors;
- a pressure responsive instrument having an input for connection to said pressure signal, said pressure responsive instrument comprising a balanced beam manometer having an output data shaft driven by a motor to balance the beam;
- drive means connected to said output data shaft to produce a drive signal responsive to rotation of said data shaft, said drive means including variable compensation means for varying said drive signal by a predetermined compensation factor corresponding to said errors in said pressure signal; and
- data acquisition means responsive to said compensated drive signal to produce a readout proportional to pressure at said submerged level.

* * * * *